United States Patent [19]

Barr

[11] Patent Number: 6,068,994
[45] Date of Patent: May 30, 2000

[54] UBIQUITIN EXPRESSION SYSTEM

[75] Inventor: Philip J. Barr, Oakland, Calif.

[73] Assignee: Chiron Corporation, Emeryville, Calif.

[21] Appl. No.: 08/428,278

[22] Filed: Apr. 25, 1995

Related U.S. Application Data

[63] Continuation of application No. 07/957,627, Oct. 6, 1992, abandoned, which is a continuation of application No. 07/806,813, Dec. 6, 1991, abandoned, which is a continuation of application No. 07/390,599, Aug. 7, 1989, abandoned.

[51] Int. Cl.[7] .......................... C07K 19/00; C12M 15/62
[52] U.S. Cl. ................. 435/69.7; 435/252.3; 435/320.1; 435/255; 530/350; 536/23.4
[58] Field of Search ................ 435/69.7, 252.3, 435/320.1, 255; 530/750; 536/23.4

[56] References Cited

U.S. PATENT DOCUMENTS

| | | |
|---|---|---|
| 4,732,973 | 3/1988 | Barr et al. . |
| 4,752,576 | 6/1988 | Brake et al. ............................... 435/68 |
| 4,839,283 | 6/1989 | Kawasaki et al. ...................... 435/69.2 |
| 4,855,238 | 8/1989 | Gray et al. ............................... 435/243 |
| 5,093,242 | 3/1992 | Bachmair et al. . |
| 5,122,463 | 6/1992 | Varshavsky et al. . |
| 5,132,213 | 7/1992 | Bachmair et al. . |

FOREIGN PATENT DOCUMENTS 8802406  4/1988  WIPO .

OTHER PUBLICATIONS

Gene, 61:265–275, 1987, Cousens et al. High level expression of proinsulin in the yeast, *Saccharomyces cerevisiae*.
Virology, 167:634–638, 1988, Hizi et al. Expression of the Molonex Murine Leukemia Virus and Human Immunodeficiency Virus Integration Proteins in *E. coli*.
Bachmair et al., *Science* 234:179–186 (1986).
Varshavsky et al., *Ubiquitin* (Rechsteiner, ed) pp. 287–324, Plenum Press, New York 1988).
Varshavsky et al., *Yeast Genetic Engineering* (Barr, Brake, and Valenzuela, eds) pp. 109–143 (1989), Butterworths, New York.
Butt et al., *J Biol Chem* 263:16364–16371 (1988).
Ecker et al., *J Biol Chem* 264(13):7715–7719 (1989).
Butt et al., *Proc Natl Acad Sci USA* 86:2540–2544 (1989).
Barr et al., *Yeast* 4:S24 (Abstract) (1988), 14th International Conference on Yeast Genetics and Molecular Biology, Aug. 7–13, 1988 in Espoo, Finland.
Sabin et al., *Biotechnology* 7:705–709 (1989).
Barr et al., *Production of Recombinant DNA–Derived Pharmaceuticals in the Yeast Saccharomyces Cerevisiae*, American Chemical Society Meeting, Sep. 1988, Los Angeles, CA.
Bachmair and Varshavsky, *Cell* 56:1019–1032 (1989).
Jonnalagadda et al., *J Biol Chem* 262(36):17750–17756 (1987).
Chau et al., *Science* 243:1576–1583 (1989).
Ben–Bassat and Bauer et al., *Nature* 326:315.
Barr et al., *J Biol Chem* 268:1671–1678 (1988).
Barr et al., *Vaccine* 5:90–101 (1987).
Bialy, H. (1989) *Bio/technology* 7:649; and.
Miller et al. (1989) *Bio/technology* 7:698–704.

*Primary Examiner*—John Ulm
*Attorney, Agent, or Firm*—Roberta L. Robins; Joseph H. Guth; Robert P. Blackburn

[57] ABSTRACT

The present invention provides an improved ubiquitin fusion system for gene expression in yeast systems which allows for the regulatable high level production of heterologous proteins having destabilizing amino terminal residues. The ubiquitin fusion proteins expressed in yeast are cleaved precisely in vivo by an endogenous ubiquitin-specific hydrolase to yield heterologous proteins such as human alpha-1-antitrypsin, human gamma-interferon and human immunodeficiency virus integrase protein, all of which initiate with destabilizing residues. An expression vector containing a synthetic gene for monomeric yeast ubiquitin was constructed and expressed under the control of a glucose regulatable yeast promoter. Inclusion of unique restriction sites at the 3'-end of the synthetic ubiquitin gene allows for precise in-frame insertion of heterologous genes. The system can be used to increase expression of poorly expressed proteins and to produce proteins having selective amino-terminal destabilizing residues.

77 Claims, 3 Drawing Sheets

UBIQUITIN EXPRESSION SYSTEM

This application is a continuation of application Ser. No. 07/957,627 filed on Oct. 6, 1992, now abandoned, which is a continuation of application Ser. No. 07/806,813 filed Dec. 6, 1991, now abandoned, which is a continuation of application Ser. No. 07/390,599 filed Aug. 7, 1989, now abandoned.

TECHNICAL FIELD

The present invention is directed to methods and materials useful for the production of heterologous proteins in yeast by recombinant DNA methods. More particularly, the present invention is directed to methods and materials based on the use of a ubiquitin DNA fusion cassette to improve the yield of heterologous proteins made in yeast and provide for amino terminal authentic heterologous proteins.

BACKGROUND OF THE INVENTION

It has been generally recognized that the intracellular expression of naturally secreted eukaryotic proteins in microorganisms such as bacteria or yeast, as an expressed, mature polypeptide will frequently contain an additional, obligatory, initiation codon-derived methionine residue at the amino terminus. In many situations the extra amino acid is not detrimental, yet if these proteins are used for pharmaceutical indications, immunogenicity problems associated with this additional residue can be problematic.

Subsequent to the development of the initial intracellular expression systems, where the "methionine problem" was first encountered, several methods for circumventing this problem were developed. First and foremost, the viability of heterologous secretion systems for bacteria, yeast, filamentous fungi, and insect and mammalian cells was demonstrated. Indeed, for complex high molecular weight and glycosylated proteins, mammalian cell secretion systems have been essential. Heterologous secretion has, however, tended to be much lower yielding when compared with intracellular expression, and in some cases, secretion systems have failed altogether to generate relevant quantities of recombinant protein.

Secondly, in vitro systems involving chemical removal of methionine by cyanogen bromide and specific processing of fusion proteins with aminopeptidases, enterokinase, collagenase, and factor Xa have been developed in order to retain the high yields often associated with intracellular expression systems. It would be, however, desirable to avoid the use of the additional processing steps required for the cleavage reaction.

Ubiquitin (Ub), a highly conserved 76 residue protein, is found in eukaryotes either free or covalently joined via its carboxy-terminal glycine residue to a variety of cytoplasmic, nuclear, and integral membrane proteins. The coupling of ubiquitin to such proteins serves to target that protein as a proteolytic substrate for degradation. An important component of the degradation signal in a short-lived protein is the protein's amino-terminal residue (Bachmair et al., (1986) *Science* 234:179–186). The degradative pathway whose initial steps involve amino-terminal recognition of proteolytic substrates is called the N-end rule pathway, to distinguish it from other proteolytic pathways and also from other ubiquitin-dependent processes, some of which may not involve degradation of target proteins.

Varshavsky and coworkers (Varshavsky et al., (1988) in Ubiguitin (Rechsteiner, ed) pp 287–324, Plenum Press, New York; Varshavsky et al., (1989) in *Yeast Genetic Engineering* (Barr, Brake and Valenzuela, eds) pp 109–143, Butterworths, N.Y.; and PCT WO88/02406, published Apr. 7, 1988) have shown that ubiquitin may be utilized for the production of recombinant proteins with specifically engineered amino termini. Initially, the production of bacterial beta-galactosidase derivatives, and murine dihydrofolate reductases (DHFRS) that differed exclusively at their amino-terminal residues lead to the definition of the N-end rule. According to this general rule, specific amino acids can be ranked according to the degree of stabilization, or destabilization, that they confer upon proteins when positioned at their amino termini. Specifically, in *Saccharomyces cerevisiae,* any of the stabilizing amino-terminal residues (Met, Gly, Val, Pro, Cys, Ala, Ser, Thr) confers a long (greater than 20 hr) half-life on the test protein beta-galactosidase, whereas destabilizing amino-terminal residues (Ile and Glu, about 30 min; His, Tyr and Gln, about 10 min; Asp, Asn, Phe, Leu, Trp and Lys, about 3 min; and Arg, about 2 min) confer on beta-galactosidase half-lives from less than 3 min to 30 min.

Bachmair et al., supra in their N-end rule work described above, showed the capacity of the endogenous yeast processing enzyme to accurately cleave Ub from heterologous fusion proteins containing any of the 20 amino acids at the Ub-protein junction. Only in the case of proline was this process slow enough to observe Ub-fusion intermediates. For accurate determination of half-lives of the amino-terminally mutated test proteins (a beta-galactosidase derivative and dihydrofolate reductase) it was important to avoid such complications as inclusion body formation and this was achieved by the use of a relatively weak promoter system.

More recently, Butt et al., (1988) *J Biol Chem* 263:16364–16371 describe studies of ubiquitin fused with a homologous yeast protein, metallothionein. The hybrid gene is under control of the yeast metallothionein promoter, a promoter of intermediate strength. Ecker et al., (1989) *J Biol Chem* 264(13):7715–7719 also describe the use of the yeast metallothionein promoter to increase ubiquitin fused gene expression of $G_8$alpha, sCD4, and the protease domain of human urokinase in yeast while Butt et al., *Proc Natl Acad Sci USA* 86:2540–2544 (1989) describe a similar ubiquitin expression system developed for use in *E. coli.*

It would be desirable to develop a yeast expression vector system, preferably an inducible system, for expression of ubiquitin fusion proteins with simultaneous in vivo processing to yield authentic biologically active proteins having destabilizing amino terminal residues.

It would also be desirable to develop a general method using this vector system for quantitative processing of ubiquitin fusions to produce high expression levels of the desired heterologous protein in a yeast host.

In furtherance of these objectives, Barr et al., (1988) *Yeast* 4:S24 (Abstract) and Sabin et al., (1989) *Biotechnology* 7:705–709 have extended the observations by Varshavsky and, using strong and regulatable promoters, have produced in yeast high levels of heterologous eukaryotic proteins. Surprisingly, all of the proteins initiate with residues that are known to be destabilizing, yet, with one exception, each of the proteins expressed using the ubiquitin vector system were found to be correctly processed. The results of this work are reproduced herein.

SUMMARY OF THE INVENTION

Methods and compositions are provided for the high fidelity production in yeast hosts of heterologous proteins having destabilizing amino terminal residues. A ubiquitin fusion expression system is provided wherein ubiquitin fusion proteins are cleaved precisely in vivo by an endogenous ubiquitin-specific hydrolase to yield heterologous proteins such as human alpha-1-antitrypsin, human gamma-interferon and human immunodeficiency virus integrase protein, all of which initiate with destabilizing residues.

In embodiment, the present invention provides a method of producing a selectively processed recombinant eukaryotic protein in yeast wherein said eukaryotic protein is encoded by a ubiquitin-heterologous hybrid gene, which method comprises:

(a) constructing a hybrid gene expression cassette comprising a first DNA sequence encoding a promoter-ubiquitin expression cassette ligated in translational reading phase, immediately adjacent to and downstream from a second DNA sequence encoding an heterologous eukaryotic protein, wherein the first codon of said second DNA sequence encodes a selective destabilizing amino acid;

(b) transforming a yeast host cell with a yeast expression vector comprising the hybrid gene expression cassette of step (a); and (c) culturing the transformed yeast host cell under conditions capable of expressing the ubiquitin-heterologous hybrid gene whereby in vivo processing of the fusion protein yields the recombinant heterologous protein having the selective destabilizing amino terminus.

The recombinant heterologous protein may be recovered from the transformed cell culture and purified.

In yet another embodiment, the invention employs the ubiquitin fusion system to increase the expression levels of eukaryotic proteins. The present ubiquitin fusion approach thus not only leads to greatly increased levels of protein expression but also provides increased expression of quantitatively processed heterologous proteins.

Other embodiments will also be readily apparent to those of ordinary skill in the art.

BRIEF DESCRIPTION OF THE DRAWINGS

FIG. 1 is a schematic representation of the ubiquitin fusion expression plasmid pBS24UbX. The parent vector pBS24Ub contains selectable markers for yeast growth in uracil- or leucine-deficient media. The promoter-ubiquitin "cassette" is cloned as a BamHI(B)-SalI(L) fragment. Heterologous genes (X) are cloned into pBS24Ub as SstII(S)/SalI fragments. Precise junction sequences are shown in FIG. 2.

FIG. 3 is a Coomassie blue-stained 15–22% gradient (a) and 12.5% gradient (b) SDS-polyacrylamide gels of heterologous proteins expressed in yeast.

DETAILED DESCRIPTION OF THE INVENTION

The practice of the present invention will employ unless otherwise indicated, conventional molecular biology, microbiology, and recombinant DNA techniques within the skill of the art. Such techniques are explained fully in the literature. See e.g., Maniatis, Fritsh & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S.J. Higgins eds. 1985); "Transcription and Translation" (B. D. Hames & S. J. Higgins eds. 1984); "Animal Cell Culture" (R. I. Freshney ed. 1986); "Immobilized Cells and Enzymes" (IRL Press, 1986); B. Perbal, "A Practical Guide To Molecular Cloning" (1984).

In describing the present invention, the following terminology will be used in accordance with the definitions set out below.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either its single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 51 to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence or, as used in the present invention, at the 3' end of the fusion protein's coding sequence.

"Transcriptional and translational control sequences" are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences. Preferred promoters for use in the present invention are strong and regulatable.

A coding sequence is "under the control" of transcriptional and translational control sequences in a cell when RNA polymerase transcribes the coding sequence into mRNA, which is then translated into the protein encoded by the coding sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. The cell has been stably transformed when the cell is able to establish cell lines or clones comprised of a population of daughter cells containing the transforming DNA. A "clone" is a population of cells derived from a single cell or common ancestor by mitosis. A "cell line" is a clone of a cell that is capable of stable growth in vitro for many generations.

Two DNA sequences are "substantially homologous" when at least about 85% (preferably at least about 90%, and most preferably at least about 95%) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

"Eukaryotic" as used herein with reference to heterologous proteins are non-yeast proteins and include mammalian- and viral-derived material. Usually, the eukaryotic polypeptide sequence will be at least about 8 amino acids in length and can include polypeptides up to about 100,000 daltons or higher. Of particular interest are polypeptides of from about 5,000 to about 150,000 daltons, more particularly of about 5,000 to about 100,000 daltons.

The term "analog" includes muteins, fusion proteins comprising domains of the desired polypeptide, and fragments. Examples of analogs which fall within the scope of the present invention include cysteine substitutions to facilitate protein purification and refolding, methionine substitution to reduce a proteins's susceptibility to oxidation, and lysine residue substitution to improve protein stability. Preferred analogs have biological activity. A mutein is a protein substantially homologous to a native sequence of the desired polypeptide (e.g., a minimum of about 75%, 85%, 90% or 95% homologous) wherein at least one amino acid is different. The term fusion protein includes a protein comprising the complete native sequence of the desired polypeptide or a functional domain or the protein, and a heterologous N- or C-terminal sequence (such as a signal sequence or sequence which protects the protein from degradation). A fragment or domain is an amino acid sequence of sufficient length from the desired polypeptide such that it is identifiable as having been derived from such a polypeptide. The origin of a particular peptide can be determined, for example, by comparing its sequence to those found in public databases.

Fragment analogs can be produced by, e.g., expression truncated coding sequences. Synthetic DNA sequences allow convenient construction of genes which will express fragments or muteins. Alternatively, DNA encoding muteins can be made by site-directed mutagenesis of native genes or cDNAs. Analogs exhibiting "biological activity" may be identified by the in vivo and/or in vitro assays, such as described in the examples of alpha-1-antitrypsin, gamma-interferon, and the HIV-1 integrase and envelope proteins.

As used herein, "destabilizing amino acids" or "destabilizing residues" refers to the set of amino-terminal residues (unblocked) that confer on beta-gal half-lives from less than 3 min to 30 min, in *S. cerevisiae* at 30° C., insert isoleucine, glutamic acid, histidine, tyrosine, glutamine, aspartic acid, asparagine, phenylalanine, leucine, tryptophan, lysine, and arginine, as defined by the N-end rule formulated by Bachmair et al., supra.

An expression vector is constructed according to the present invention so that the ubiquitin-heterologous protein coding sequence is located in the vector with the appropriate regulatory sequences, the positioning and orientation of the hybrid gene coding sequence with respect to the control sequences being such that the hybrid gene coding sequence is transcribed and translated under the control of the control sequences. The control sequences may be ligated to the coding sequence prior to insertion into a vector as taught below. Alternatively, the coding sequence can be cloned directly into an expression vector which already contains the control sequences and an appropriate restriction site. For expression of a heterologous protein in yeast, the control sequences will necessarily be heterologous to the coding sequence.

An "expression cassette" is a DNA construct comprising a coding sequence under the control of transcription initiation and termination sequences. In the practice of the present invention, such constructs will involve bacterial-derived or yeast-recognized transcription and termination sequences, and, for example, a coding sequence for the ubiquitin gene or alternatively, a ubiquitin-heterologous fused gene construction. It is particularly preferred to flank the expression cassettes with restriction sites that will provide for the convenient cloning of the cassettes into an appropriate vector.

The promoter-ubiquitin expression construct of the invention provides a portable sequence for insertion into vectors, which provide the desired replication system. In yeast, promoters involved with enzymes in the glycolytic pathway can provide for high rates of transcription. These promoters are associated with such enzymes as phosphoglucoisomerase, phosphofructokinase, phosphotriose isomerase, phosphoglucomutase, enolase, pyruvic kinase, glyceraldehyde-3-phosphate dehydrogenase (GAPDH), alcohol dehydrogenase(ADH 1 and 2), as well as hybrids of these promoters. A particularly preferred hybrid promoter is the hybrid formed from the 5' regulatory sequences of the ADH2 gene (including the upstream enhancer sequence) and the GAPDH promoter transcription initiation site and consensus sequences, referred to as a "ADH2/GAPDH hybrid promoter." See, e.g., EPO Publication Nos. 120,551; 164,556; 196,056. In like manner, a transcription terminator sequence located 3' to the translation stop codon can be yeast-recognized termination sequences, such as those from the genes for other glycolytic enzymes.

The heterologous gene may encode for any type of polypeptide of interest. Clinically and veterinary important genes that may be employed in the invention include, for example, genes encoding hormones and growth factors, such as growth hormone, somatomedins, epidermal growth factor, fibroblast growth factors, insulin, nerve growth factor, vasopressin, renin, calcitonin, erythropoietin, colony-stimulating factors, lymphokines such as interleukin-2, globins, immunoglobins, interferons (e.g., alpha, beta or gamma), enzymes, etc. Representative viral proteins include those from the human immunodeficiency virus (e.g., envelope, integrase, and gag precursor). Preferred embodiments include human gamma-interferon, human alpha-1-antitrypsin and the integrase protein of the human immunodeficiency virus (HIV).

The genes encoding the heterologous proteins of interest may be synthetic or natural, or combinations thereof. A natural gene (or portion thereof) may be obtained by preparing a cDNA or genomic library and screening for the presence of the gene of interest. Preparation of CDNA libraries from a messenger RNA population is well known and described fully in Huynh et al, (1984) in DNA cloning, Vol. 1: A Practical Approach (D. Glover, ed.), pp. 49–78, IRL Press, Oxford.

When preparing a synthetic nucleotide sequence, it may be desirable to modify the natural nucleotide sequence. For example, it will often be preferred to use codons which are preferentially recognized by the desired host. In some instances, it may be desirable to further alter the nucleotide sequence to create or remove restriction sites to, for example, enhance insertion of the gene sequence into convenient expression vectors or to substitute one or more amino acids in the resulting polypeptide to increase stability. A general method for site-specific mutagenesis is described in Noren et al., (1989), *Science* 244:182–188. This method may be used to create analogs with unnatural amino acids.

Synthetic oligonucleotides are prepared by either the phosphotriester method as described by Duckworth et al., (1981) *Nuc Acids Res* 9:1691 or the phosphoramidite method as described by Beaucage and Caruthers, (1981) *Tet Letts* 22:1859 and Matteucci and Caruthers, (1981) *J Am Chem Soc* 103:3185, and can be prepared using commercially available automated oligonucleotide synthesizers, such as the Applied Biosystems 380A DNA synthesizers.

Adaptor sequences may be necessary to fuse the ubiquitin and heterologous gene sequences in-frame at the junction site to generate the specific processing site recognized by the endogenous yeast endoprotease. A yeast hydrolase responsible for this cleavage has been characterized at the molecular level by cloning and over expression of its gene product (Miller et al., (1989) *Biotechnology* 7: 831). The yeast hydrolase cleaves the junction peptide bond between the C-terminal $Gly_{76}$ of ubiquitin and the heterologous fusion protein rapidly in all cases, except when the first amino acid of the extension protein is proline.

The vector construct will be an episomal element capable of stable maintenance in a host, particularly a fungal host such as yeast. The construct will include one or more replication systems, desirably two replication systems allowing for maintenance of the replicon in both a yeast host for expression and a bacterial (e.g., *E. coli*) host for cloning. Numerous cloning vectors are known to those of skill in the art. They may be used as intermediates in the construction of replicable expression vectors, or as integrating expression vectors, when the intended expression host does not recognize the cloning vector's origin of replication. Examples of recombinant DNA vectors for cloning and host cells which they can transform include the various bacteriophage lambda vectors (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), actinophage and phiC31 (Streptomyces). Examples of such yeast-bacteria shuttle vectors include YEp24 [Botstein et al., *Gene* 8:17–24], pC/i [Brake et al., (1984) *Proc Natl Acad Sci USA* 81:4643–4646], and YRpl7 [Stinchomb et al., (1982) *J Mol Biol* 158:157]. See generally, DNA Cloning: Vols. I & II, supra; T. Maniatis et al., supra; B. Perbal, supra.

Furthermore, an extra-chromasomal vector may be a high or low copy number vector, the copy number generally ranging from about 1 to about 500. High copy number plasmids may be employed as one means to promote the high level expression of the heterologous proteins of the invention. With high copy number yeast vectors, there will generally be at least 10, preferably at least 20, and usually not exceeding about 150–500 copies in a single host. DNA constructs of the present invention can also be integrated into the yeast genome by an integrating vector. Examples of such vectors are known in the art as shown by Botstein et al., supra. Preferably, less than 50 copies of the cassette are integrated into the genome, more preferably less than about 10, and usually less than about 5. Typically, only 1 or 2 copies are integrated.

The selection of suitable yeast and other micro-organism hosts (e.g., diploid, haploid, auxotrophs, etc.) for the practice of the invention is within the skill of the art. When selecting yeast hosts for expression, suitable hosts may include those shown to have, inter alia, good secretion capacity, low proteolytic activity, and overall robustness. Integrating yeast vectors will not contain an origin of replication recognizable by the yeast host. Replicating yeast vectors generally will contain an origin of replication from the 2 micron yeast plasmid or an autonomously replicating sequence (ARS). The yeast vectors will also typically contain a gene encoding a selectable marker used to confirm transformation, as well as an origin of replication recognizable by a non-yeast host, such as bacteria for convenient cloning. Yeast and other microorganisms are available from a variety of sources, including the Yeast Genetic Stock Center, Department of Biophysics and Medical Physics, University of California, Berkeley, Calif.; and the American Type Culture Collection, Rockville, Md. Yeast expression vectors are known in the art. See, e.g., U.S. Pat. Nos. 4,446,235; 4,443,539; 4,430,428; see also European Pub. Nos. 103,409; 100,561; 96,491.

Methods of introducing exogenous DNA into microbial hosts are well known in the art. There is a wide variety of ways to transform yeast. For example, spheroplast transformation is taught by Hinnen et al., (1978) *Proc Natl Acad Sci USA* 75:1919–1933 and Stinchomb et al., EP Publication 45,573. The calcium chloride treatment as described by Cohen, et al., (1972) *Proc Natl Acad Sci USA* 69:2110, or the RbCl$_2$ method described in Maniatis, et al, supra may be used for procaryotes or other cells which contain substantial cell wall barriers. Transformants are grown in an appropriate nutrient medium, and, where appropriate, maintained under selective pressure to insure retention of endogenous DNA. Where expression is inducible, growth can be permitted of the microbial host to yield a high density of cells, and then expression is induced. The heterologous protein is then isolated from cell lysates and purified.

As used herein, a "selectively processed protein" refers to a protein that is quantitatively processed from the ubiquitin fusion protein to yield a free recombinant heterologous protein having an amino-terminus identical to that of the selected codon in the DNA encoding the heterologous protein.

"High level expression" or "increased expression" refers to the yield of heterologous protein determined from a microbial cell lysate and calculated as a percentage of total cell protein. Quantitation of protein yield may be determined by densitometric scanning of protein bands on a polyacrylamide gel or by alternative methods such as, for example, quantitation using a purified yeast-derived or bacterial-derived protein standard and quantitation of the total soluble proteins by Lowry protein assay. At minimum, high level expression refers to a level of at least 5% of total cell protein, more preferably in the range of about 10 to about 50% of total cell protein, and most preferably in the range of about 10 to about 30% total cell protein.

The heterologous protein can be harvested by any conventional means. In the case of yeast expression, in vivo cleavage of the ubiquitin heterologous fusion protein occurs to provide quantitatively processed "authentic" amino terminal proteins. The desired heterologous protein may be purified by employing conventional purification techniques. Such techniques include, but are not limited to size exclusion chromatography, ion-exchange chromatography, HPLC, electrophoresis, dialysis, solvent-solvent extraction, and the like.

As demonstrated herein and in the art, specific cellular mechanisms exist for the amino terminal modification of proteins prior to degradation via the N-end rule pathway. The existence of these modification pathways has several implications for heterologous gene expression using the ubiquitin fusion approach. Human gamma-interferon and alpha-1-antitrypsin have tertiary (Gln) and secondary (Glu) destabilizing amino acids respectively at their amino termini. It has been shown previously by Varshavsky and coworkers, that amino-terminal Gln and Asn can be hydrolyzed to Glu and Asp residues respectively. The secondary destabilizing residues, Glu, Asp and Cys can be modified by arginyl-RNA-protein-transferase catalyzed addition of Arg, a primary destabilizing amino acid to the amino terminus of a substrate protein. The definite possibility existed therefore that the amino terminal residue could be modified by the addition of Arg, to differ from the native sequence. Indeed, sequence analysis of one of the human immunodeficiency viral proteins, env4, expressed using the system of the present invention gives a heterogeneous final product.

The mechanisms for increased expression using the ubiquitin fusion approach of the present invention are unresolved. Several mechanisms that could account for the observed increase include, for example: increased transcription or message stability; increased mRNA translatability, cellular compartmental targeting by the yeast ubiquitin fusion partner; or a combination of these factors. Moreover, for any given protein, a variety of factors in addition to the N-end rule may combine to modulate its half-life in vivo. Among such factors may be the solubility or insolubility of a protein, the flexibility and accessibility of the protein's amino terminus, the distribution of ubiquitinatable lysine residues near the amino terminus, and the presence of chemically blocking amino terminal groups. Surprisingly, the amino termini of many of the proteins exemplified in the present invention are amino acids of the destabilizing class according to the N-end rule. While the present invention does not delineate the mechanism(s) responsible for increased expression, it does provide a means to achieve such desirable ends.

EXAMPLES

The following examples are provided for illustrative purposes only, and are not intended to limit the scope of the present invention.

The ubiquitin fusion system of yeast expression was tested with a variety of proteins: human gamma interferon, alpha-1-antitrypsin, HIV-1 integrase and envelope proteins. In all instances a high level of expression was observed.

The Ubiguitin Fusion Expression Vector

The yeast *Saccharomyces cerevisiae* ubiquitin gene encoding a 76 amino acid polypeptide (Ozkaynak et al., *Nature* 312:663–666 (1984)) was synthesized by an Applied Biosystem 380A using the method in Barr et al., *J Biol Chem* 268:1671–1678 (1988) as a fragment with NcoI (non-regenerated) and SalI cloning sites at the 5' and 3' termini, respectively. The amino acid and DNA sequences are as follows:

```
    1                           10

MetGlnIlePheValLysThrLeuThrGlyLysThrIleThrLeuGlu

ATGCAGATCTTCGTCAAGACTTTGACCGGTAAAACCATAACATTGGAA

TACGTCTAGAAGCAGTTCTGAAACTGGCCATTTTGGTATTGTAACCTT 16                          25

ValGluSerSerAspThrIleAspAsnValLysSerLysIleGln

GTTGAATCTTCCGATACCATCGACAACGTTAAGTCGAAAATTCAA

CAACTTAGAAGGCTATGGTAGCTGTTGCAATTCAGCTTTTAAGTT 31                          40

AspLysGluGlyIleProProAspGlnGlnArgLeuIlePheAla

GACAAGGAAGGTATCCCTCCAGATCAACAAAGATTGATCTTTGCC

CTGTTCCTTCCATAGGGAGGTCTAGTTGTTTCTAACTAGAAACGG 46                          55

GlyLysGlnLeuGluAspGlyArgThrLeuSerAspTyrAsnIle

GGTAAGCAGCTAGAAGACGGTAGAACGCTGTCTGATTACAACATT
```

-continued

```
CCATTCGTCGATCTTCTGCCATCTTGCGACAGACTAATGTTGTAA 61                              70

GlnLysGluSerThrLeuHisLeuValLeuArgLeuArgGlyGly

CAGAAGGAGTCCACCTTACATCTTGTGCTAAGGCTCCGCGGTGGT

GTCTTCCTCAGGTGGAATGTAGAACACGATTCCGAGGCGCCACCA

76

SalI

TAGTCGAC

ATCAGCTG
```

For construction of chimeric genes, a unique SstII site was incorporated at the 3'-end of the Ub gene and a unique SalI site immediately subsequent to the Ub termination codon. Genes for heterologous proteins may be inserted, together with appropriate adaptors, at these sites using BamHI sites close to the 5'-termini of the synthetic or natural genes.

The NcoI-SalI fragment was cloned by a two-step method into pBS24, a plasmid which is described in copending U.S. patent application Ser. No. 138,894, filed December 24, 1987. Briefly, plasmid pAB24 was used as the starting material in the construction of pBS24, a yeast shuttle vector which contains the complete 2-micron sequence [Broach, in: *Molecular Biology of the Yeast Saccharomyces*, Vol. 1, p. 445, Cold Spring Harbor Press (1981)] and pBR322 sequences. This vector also contains the yeast URA3 gene derived from plasmid YEp24 [Botstein et al. *Gene* 8:17 (1979)] and the yeast LEU2d gene derived from plasmid pCI/1 (See EP Publication 116,201). Plasmid pAB24 was constructed by digesting YEp24 with EcoRI and religating the vector to remove the partial 2-micron sequences. The resulting plasmid, YEp24deltaRI, was linearized by digestion with ClaI and ligated with the complete 2-micron plasmid which had been linearized with ClaI. The resulting plasmid, pCBou, was then digested with XbaI, and the gel purified 8605 bp vector fragment was ligated with a 4460 bp XbaI fragment containing the LEU2d gene isolated from pCl/1; the orientation of the LEU2d gene is in the same direction as the URA3 gene. Insertion of the expression cassette was in the unique BamHI site of the pBR322 sequences, this interrupting the gene for bacterial resistance to tetracycline.

Plasmid pAB24 was subsequently digested with BamHI and SalI (which cut within the tetracycline gene of the pBR322 sequences) and gel purified. The vector was then ligated with a synthetic adapter of the following sequence which created new unique BglII and BamHI sites:

```
          BglII           BamHI
5'-GATCAGATCTAAATTTCCCGGATCC-3'
         TCTAGATTTAAAGGGCCTAGGAGCT
 (BamHI)                       (SalI)
```

The resulting vector, pAB24deltaBL, was then digested with BamHI and BglII, gel purified and ligated with the excised BamHI cassette to give pBS24. The cassette contains, inter alia, the hybrid ADH2-GAPDH promoter and alpha-factor terminator. The cassette is oriented in pBS24 such that the direction of transcription from the ADH2-GAPDH promoter is in the opposite direction to that of the inactivated tetracycline gene of the pBR322 sequences.

Figure 1:
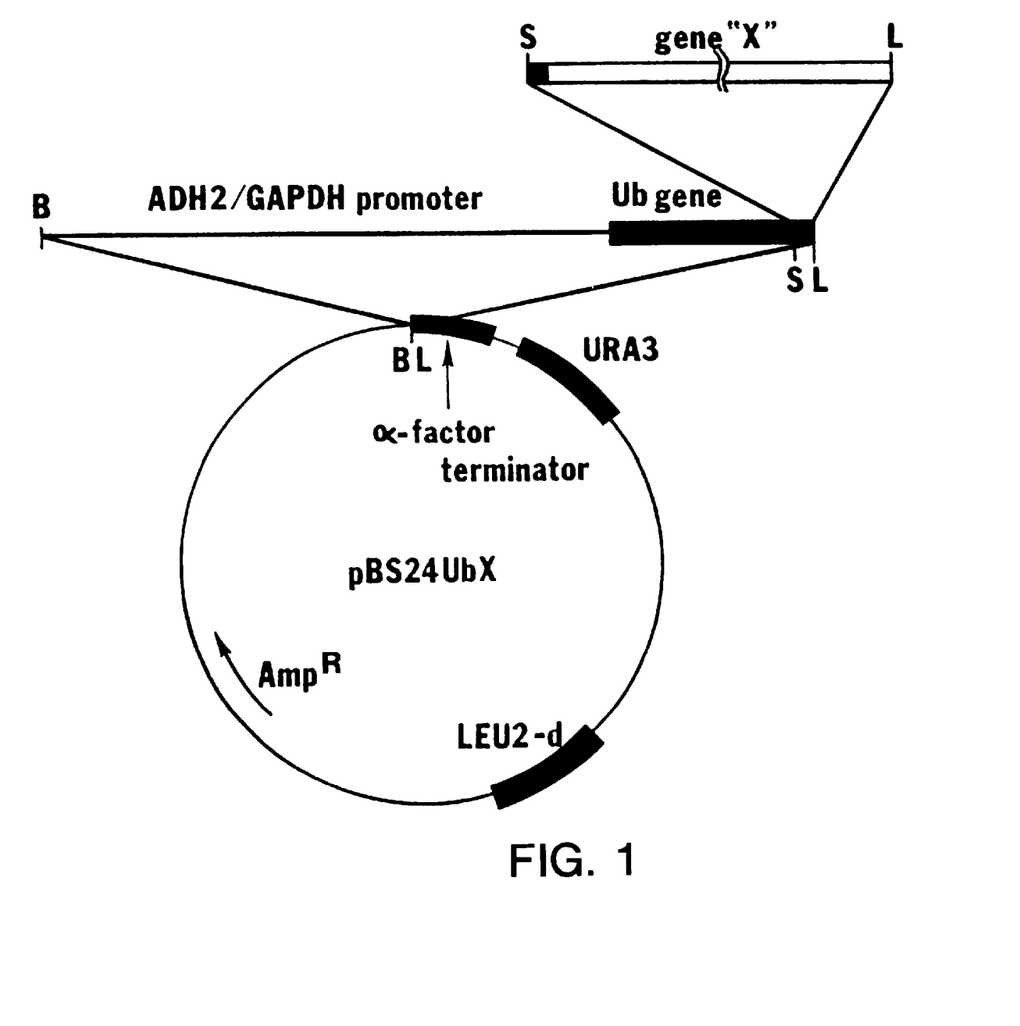
Figure 2:
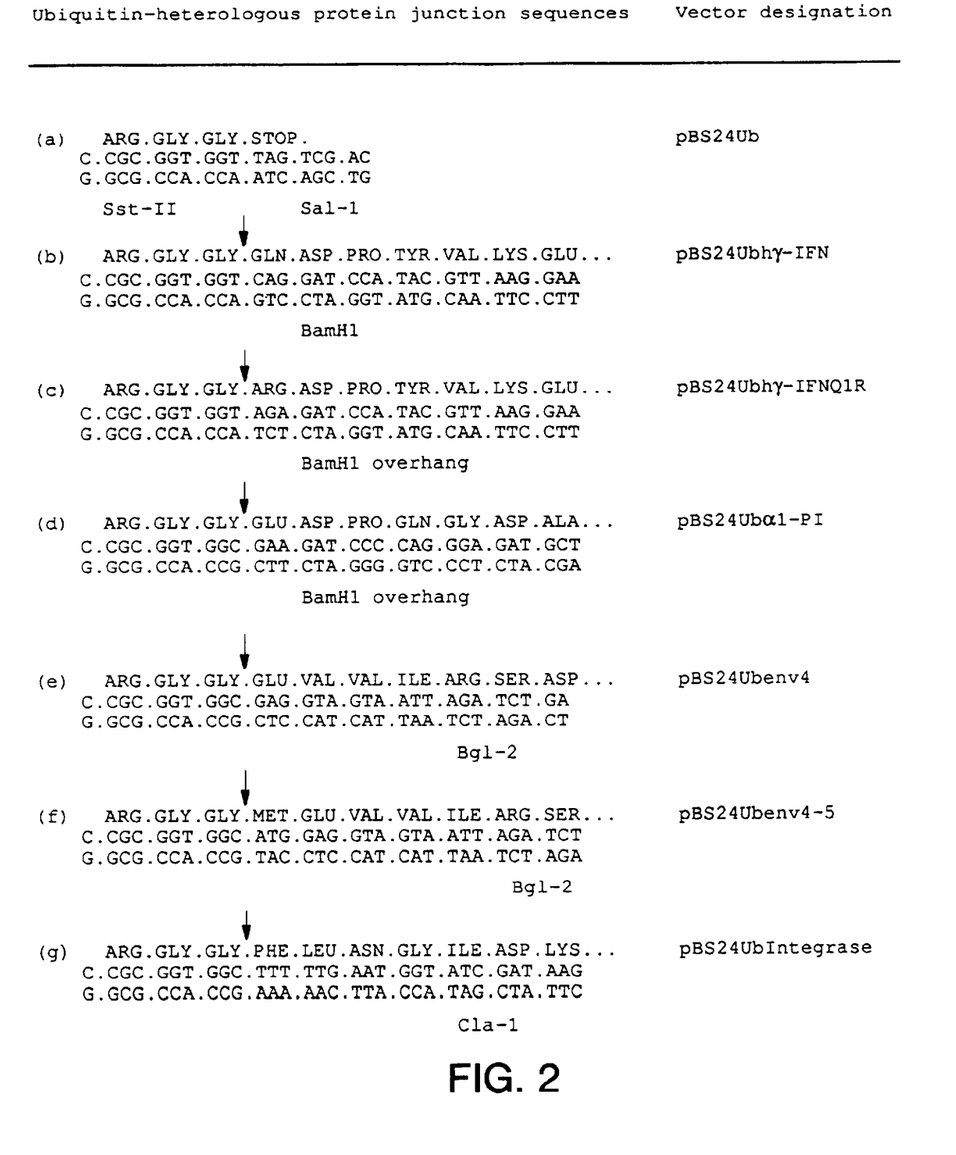
FIG. 2 illustrates the synthetic DNA (boxed) and encoded amino acid sequences at ubiquitin-heterologous gene and protein junctions. The fusion protein cleavage site is shown by the arrow above each protein sequence.

The first step in the construction of the ubiquitin fusion expression vector of the present invention involved the ligation of the ubiquitin NcoI/SalI fragment into a pBS100 NcoI/SalI vector fragment (described below). Next, a BamHI/SalI fragment (containing the ADH2-GAPDH promoter and ubiquitin gene) was isolated from the new pBS100/ubiquitin plasmid and ligated to the BamHI/SalI vector fragment of pBS24. The resulting ubiquitin fusion is under the control of the ADH2-GAPDH promoter (see U.S. Pat. No. 4,876,197, ) and the alpha-factor terminator (Barr et al., (1987) *Vaccine* 5:90–101). The resulting vector, pBS24UbX, contains unique SstII and SalI restriction sites for insertion of heterologous proteins. A schematic representation of this ubiquitin fusion expression vector is provided in FIG. 1.

Plasmid pBS100 contains a yeast expression cassette cloned into a pBR322 derivative, pAB12. The expression cassette contains the hybrid ADH2/GAPDH promoter and the GAPDH terminator flanking a non-essential gene segment. The ADH2-GAPDH promoter is a 1200 bp BamHI-NcoI fragment and the GAPDH terminator is a 900 bp SalI-BamHI fragment (see EP Publication 164,556, supra). Plasmid pBS100 also contains a non-essential fragment between NcoI and SalI sites which is replaced by gene fragments of interest. The expression cassette can be removed from pBS100 by digestion with BamHI and cloned into yeast shuttle vectors for introduction into yeast cells.

Heterologous Genes

The human gamma interferon is a synthetic gene made by the protocol described in Barr et al., *J Biol Chem,* supra. Both the DNA and amino acid sequences are provided below:

```
1                               10

LeuAspLysArgCysTyrCysGlnAspProTyrValLysGluAla

CTAGATAAAAGATGTTACTGTCAGGATCCATACGTTAAGGAAGCT

GATCTATTTTCTACAATGACAGTCCTAGGTATGCAATTCCTTCGA 16                              25

GluAsnLeuLysLysTyrPheAsnAlaGlyHisSerAspValAla

GAAAACCTAAAGAAATACTTCAACGCTGGTCACTCTGACGTTGCT

CTTTTGGATTTCTTTATGAAGTTGCGACCAGTGAGACTGCAACGA 31                              40

AspAsnGlyThrLeuPheLeuGlyIleLeuLysAsnTrpLysGlu

GACAACGGTACCTTGTTCTTGGGTATCTTGAAAAACTGGAAGGAA

CTGTTGCCATGGAACAAGAACCCATAGAACTTTTTGACCTTCCTT 46                              55

GluSerAspArgLysIleMetGlnSerGlnIleValSerPheTyr
```

-continued

```
GAATCTGACAGAAAGATCATGCAATCCCAAATCGTTTCTTTCTAC
CTTAGACTGTCTTTCTAGTACGTTAGGGTTTAGCAAAGAAAGATG
```

61                          70

PheLysLeuPheLysAsnPheLysAspAspGlnSerIleGlnLys

```
TTCAAGTTGTTCAAGAACTTCAAGGACGACCAATCTATCCAAAAG
AAGTTCAACAAGTTCTTGAAGTTCCTGCTGGTTAGATAGGTTTTC
```

76                          85

SerValGluThrIleLysGluAspMetAsnValLysPhePheAsn

```
TCTGTTGAAACCATCAAGGAAGACATGAACGTTAAGTTCTTCAAC
AGACAACTTTGGTAGTTCCTTCTGTACTTGCAATTCAAGAAGTTG
```

91                          100

SerAsnLysLysLysArgAspAspPheGluLysLeuThrAsnTyr

```
TCTAACAAGAAGAAGAGAGACGACTTCGAAAAGCTTACCAACTAC
AGATTGTTCTTCTTCTCTCTGCTGAAGCTTTTCGAATGGTTGATG
```

106                         115

SerValThrAspLeuAsnValGlnArgLysAlaIleHisGluLeu

```
TCTGTTACCGACTTGAACGTTCAAAGAAAGGCTATCCACGAATTG
AGACAATGGCTGAACTTGCAAGTTTCTTTCCGATAGGTGCTTAAC
```

121                         130

IleGlnValMetAlaGluLeuSerProAlaAlaLysThrGlyLys

```
ATCCAAGTTATGGCTGAATTGTCTCCAGCTGCTAAGACCGGTAAG
TAGGTTCAATACCGACTTAACAGAGGTCGACGATTCTGGCCATTC
```

136                         145

ArgLysArgSerGlnMetLeuPheArgGlyArgArgAlaSerGln

```
AGAAAGAGATCTCAAATGTTGTTCAGAGGTAGAAGAGCTTCTCAA
TCTTTCTCTAGAGTTTACAACAAGTCTCCATCTTCTCGAAGAGTT

TAATAGCGTCGTCGAC
ATTATCGCAGCAGCTG
```

The alpha-1-antitrypsin CDNA was retrieved from a cDNA library as taught by Rosenberg et al., *Nature* 312:77–79 (1984) and in U.S. Pat. No. 4,732,973. The teachings of both of these references are incorporated herein by reference.

HIV-1 DNA was obtained from previously manipulated subclones of the proviral genome of the SF-2 strain of HIV-1, into which SalI sites were inserted immediately subsequent to the relevant termination codons, according to the teachings of Barr et al., *Vaccine* (1987), supra and Steimer et al., *J Virol* 58:9–16 (1986).

The gene for env4 encodes amino acids 272–509 of the env gene product and therefore corresponds to the carboxy-terminal half of gp120. The longer env4–5 gene encodes amino acids 272 to 673 of the env gene product and, therefore, includes 174 amino acids of gp41. The HIV-1 SF-2 env4 is also described in copending U.S. patent application Ser. No. 138,894, filed Dec. 24, 1987, which is incorporated herein by reference. The ubiquitin junction sequences were made using a unique BglII site for env 4 and env4–5, together with the synthetic adaptors shown below.

Similarly, a synthetic adaptor, described below, was used to fuse the ubiquitin and HIV integrase genes at the SstII site of ubiquitin and an engineered ClaI site at the Ile5 of integrase. The DNA sequence of the integrase gene is provided in U.S. Pat. No. 5,156,949, supra, and in Light-foote et al., *J Virol* 60:771–775 (1986).

Cloning Ubiguitin Fusions

To clone into the ubiquitin vector, pBS24Ub, each of the heterologous genes to be expressed must start with a unique 5' SstII site and end with a unique 3' SalI site.

The genes in these examples have had their stop codons mutagenized to a TAG stop codon. Then a SalI site, GTCGAC, was added adjacent to and downstream from the G of the TAG stop codon. The following linkers were made for the ubiquitis gene and the 5' each of the heterologous gen genes expressed to create an SstII site at the 3' end of each heterologous gene:

(a) Human gamma interferon: GGT GGT CAG CG CCA CCA GTC CTA G (b) HIV env segment: GGT GGC GAG GTA ATT A CG CCA CCG CTC CAT TAA TCT AG (c) HIV integrase: GGT GGC TTT TTG AAT GGT AT CG CCA CCG AAA AAC TTA CCA TAG C (d) Alpha-1-antitrypsin: GG GTT AAC CGC GGT GGC GAA CC CAA TTG GCG CCA CCG CTT CTA G All synthetic DNA constructions were verified by M13 dideoxy sequencing (Sanger et al., *Proc Natl Acad Sci USA* 74:5463–5466 (1977)), and plasmid preparations and enzyme reaction were essentially performed according to the methodology described in Maniatis et al., (1982) *Molecular Cloning: A Laboratory Manual,* Cold Spring Harbor Laboratory, Cold Spring Harbor, N.Y. *E. coli* strains HB101 and D1210 were used for gene cloning and plasmid amplification. Restriction enzymes, T4 polynucleotide kinase and T4 DNA ligase were obtained from NEB and BRL.

Expression of Ubiguitin Fusions

The yeast strains *S. cerevisiae* AB116, Mat-alpha leu2 trpl ura3–52 prBl-1122 pep4–3 prCl-407 [cir ] and JSC302, an ADR1 overexpressing derivative of AB116 (Shuster, J.R. (1989) in *Yeast Genetic Engineering,* pp. 83–108, Butterworths, N.Y.), were used exclusively. Yeast cells were transformed by the spheroplast method, Hinnen et al., *Proc Natl Acad Sci USA* 75:1919–1933 (1978), and propagated under conditions of leucine selection prior to liquid culture in YEP media (Barr et al., *J Exp Med* 165:1160–1171 (1987)). Induction of heterologous gene expression was as described in Barr et al., *J Exp Med* (1987), supra. Yeast cells transformed with the above plasmids were induced for expression by growth and concomitant depletion of glucose from the culture media.

Biological Assays

Anti-elastase Assay

To determine the anti-elastase activities of recombinant alpha-1-antitrypsin, the human leukocyte elastase assay set forth in U.S. Pat. No. 4,732,973, supra was employed. Alternatively, yeast extracts were incubated with human sputum elastase and a synthetic peptide substrate, the cleavage of which can be assayed at 405nm. For this assay, extracts (0–100 ng) were diluted in a sample buffer (50 mm Tris-Cl, pH 8, 0.5 NaCl, 100 ug/ml BSA). Aliquots were transferred to individual wells of an Immulon-2™ microtiter plate (Dynatech) containing 150 ul of the sample buffer and 3 ul of human sputum elastase (at 100 ug/ml in 50 MM NaOAc, pH 5.5). The plates were incubated at 37° C. for 15 minutes. Next, 15 ul of 10 mM Meo-Suc-Ala-Pro-Val-p-nitroanilide (Vega) in DMSO were added and the plates were incubated at 37° C. for one hour, followed by 30 minutes at room temperature. The reaction was terminated by the addition of 50 ul of 50% acetic acid and the absorption at 405 nm determined.

In all cases, the recombinant alpha-1-AT was shown to inhibit elastase stoichiometrically. Lastly, the amino-terminal authentic alpha-1-AT was shown, in a rabbit model system, to more closely mimic plasma-derived alpha-1-AT with respect to antigenicity and tissue distribution than its amino-terminal methionine-containing counterpart.

Gamma-IFN Bioassay

Recombinant gamma-IFN was assayed by the microtiter method described by Rubinstein et al., *J Virol* 37:755–758 (1981) for reduction of cytopathogenicity of vesicular stomatitis virus (VSV). Briefly, human foreskin fibroblasts ($5 \times 10^4$ cells/well) were grown in microtiter plates for 20–24 hours with serial 2-fold dilutions of IFN. About 10 plaque forming units of the Indian strain of VSV were added per well and plates incubated for 48 hours. Titers were scored as the reciprocal of the dilution in the well in which 50% of the cell monolayer was protected. Assays were standardized using beta- and gamma-IFN samples obtained from the NIH. Quantitative assessment of the antiviral activity of recombinant gamma-IFN gave specific activities of approximately $1.5 \times 10^7$ U/mg. This is comparable to the activity previously reported for recombinant gamma-IFN and for gamma-IFN purified from natural sources (Rinderknecht et al., *J Biol Chem* 259:6790–6797 (1984)).

Protein Purification

Induced yeast cultures were harvested by centrifugation (3,000 rpm for 15 min at 4° C.) and the cells were analyzed by 15–22% and 12.5% SDS polyacrylamide gels and Coomassie blue staining. Recombinant proteins were purified for analysis as follows: For N-terminal sequence analysis of gamma-IFN and the envelope and integrase proteins from the Ub vector system, yeast cells were lysed by the glass bead method (Barr et al., *J Exp Med* (1987), supra) in Triton lysis buffer (O.lM sodium phosphate, pH 7.3, 1.25 mM EDTA and 0.1% Triton X-100). The insoluble fractions were heated at 90° C. for 5 to 10 min in sample loading buffer (62.5 mM Tris-Cl, pH. 6.8, 50 mM DTT, 3% SDS, 10% glycerol, and, optionally, IXFSB), prior to separation on preparative 15–22% or 12.5% polyacrylamide gels. Proteins were electrophoretically transferred directly to Immobilon-P- membranes without gel staining according to the procedure of LeGendre and Matsudaira, *BioTechniques* 6:154–159 (1988). The region of transferred protein corresponding to the desired proteins was visualized using Coomassie blue staining, if necessary, and the protein band was excised and sequenced using an Applied Biosystems model 470A gas-phase sequencer.

For specific activity determination, amino-terminal authentic and N-methionyl-gamma-IFNs were purified by ion-exchange chromatography on Mono-S™ FPLC columns (Pharmacia).

After the cells were lysed and the protein separated from the cell debris, protein samples were diluted 1:1 in Buffer A (6.OM urea, 25mM Tris-HC1, pH 8.0, lmM EDTA, 1 ug/ml pepstatin and lmM PMSF). A Mono-S™ FPLC column (Pharmacia, 5 mm×50 mm) was equilibrated with Buffer A at 1 ml/min. Next, 250 ul of the diluted sample was loaded on the column and eluted with a 0–500mM NaCl gradient in Buffer A. During the column run, protein content was detected by monitoring absorbance at $A_{280}$. Collected fractions were analyzed by SDS-PAGE (15% concentration). Fractions containing gamma-IFN were pooled and tested for antiviral activity.

Similarly, yeast extracts containing amino-terminal authentic or N-methionyl-alpha-1-ATs were applied to a column of Cibacron Blue Sepharose (3.0×40 cm), and equilibrated with extraction buffer (0.05M Tris-HCl, 0.05M NaCl, pH 8.0). Proteins were then eluted in two major peaks by further washing of the column with buffer. The elastase inhibitory activity was associated with the leading fractions of the second peak.

Fractions containing elastase inhibitory activity from the Cibacron Blue purification were pooled and diluted with Buffer A (lOmM Tris-HCl$_1$, pH 8.0 and lmM EDTA) to a conductivity of below 4 ms/cm. Ten ml of the pooled fractions were loaded onto a 5 mm×50 mm Mono Q™ FPLC column (Pharmacia). The column was washed with Buffer A and then the protein was eluted with a 0–300mm NaCl gradient in Buffer A. Protein content was monitored by absorbance at $A_{280}$. Two ml fractions were collected at a flow rate of 1.5 ml/min and peak fractions containing elastase activity were pooled. Purity was assessed using a 12.5% SDS-PAGE gel.

The purified gamma-IFN and alpha-1-AT proteins were quantitated using the protein assay system commercially available from BioRad. This assay utilizes Coomassie blue G-250 to measure the amount of protein in solution.

Figure 3A:
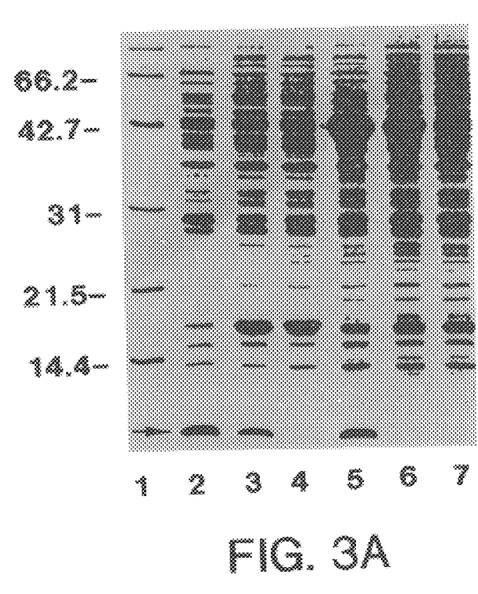
FIG. 3(a) provides in Lane 1, molecular weight standards (Biorad); Lane 2 is yeast ubiquitin (arrowed); Lane 3 is human gamma-interferon (IFN) and ubiquitin derived from in vivo cleavage of the fusion protein; Lane 4 is N-methionyl-gamma-IFN; Lane 5 is alpha-1-antitrypsin (AT) and ubiquitin from in vivo cleavage of the fusion protein; Lane 6 is N-methionyl-alpha-1-AT; Lane 7 is a control lysate from yeast cells transformed with the parent plasmid pBS24.

Expression levels of gamma-IFN and alpha-1-AT were compared when the corresponding genes were expressed directly or as chimeric Ub fusions. For corresponding direct expression, the ADH2-GPADH promoter was fused, together with synthetic adapters containing methionine initiation codons, to the 5'-termini of each gene, using the BamHI sites. SDS-PAGE analysis as shown in FIG. 3(a) showed that, as with direct expression, extremely high levels of heterologous protein were obtained in the Ub system (>25% of total protein). Lane 1 provides the prestained lower molecular weight standards (BioRad); Lane 2 is yeast ubiquitin (arrowed); Lane 3 is human gamma-IFN and ubiquitin derived from in vivo cleavage of the fusion protein; Lane 4 is N-methionyl-gamma-IFN; Lane 5 is alpha-1-AT and ubiquitin from in vivo cleavage of the fusion protein; Lane 6 is N-methionyl-alpha-1-AT; and Lane 7 is the control lysate from yeast cells transformed with the parent plasmid pBS24. Remarkably, no incompletely processed Ub fusion molecules were observed by Coomassie blue staining or, in the case of alpha-1-AT, by a more sensitive Western blot assay, indicating an extremely efficient Ub cleavage process.

Amino acid sequence analysis showed that, within the limits of experimental detection, the expressed gamma-IFN had the amino terminus Gln.Asp.Pro. . . exclusively, and the recombinant alpha-1-AT commenced with Glu.Asp.Pro. . . This was as predicted from the DNA sequence together with the known specificity of the Ub cleaving enzyme. In contrast, the results of the direct expression experiments confirmed previously published data (Travis et al., *J Biol Chem* 260:4384–4389 (1985)) that gamma-IFN and alpha-1-AT can only be produced as N-methionylated derivatives when expressed directly using similar or identical *S. cerevisiae* promoter system. This has also been reported for gamma-IFN expressed intracellularly in *E. coli* (Ben-Basset and Bauer *Nature* 326:315 (1987).

It was also noted that no additional amino-terminal modification were detected in these particular recombinant proteins. Such modifications could have included, for example, hydrolysis of the amino-terminal glutamine of gamma-IFN to glutamic acid, or the addition of arginine to the amino-terminal glutamic acid of alpha-1-AT. As noted above, these modifications have been observed previously in the appropriately modified test proteins, and are clearly the result of natural protein degradative pathways in eukaryotic cells.

Quantitation of Expression of HIV-1 Proteins

Comparative assessment of expression levels from direct, ubiquitin fusion, or hSOD fusion expression systems was obtained using a quantitative slot blot method. Reagents used for detection were from the commercially available RIBA AIDS strip kit (available from Chiron Corporation/Ortho Diagnostics). Approximately 1 ml samples of induced yeast cells were centrifuged and lysed by boiling for 5 min in 200 ul of SDS lysis buffer (150 mM Tris-Cl, pH 6.8, 2% SDS, and 3% 2-mercaptoethanol). The samples were centrifuged, and the supernatants diluted (1:62) in the provided sample diluent prior to loading onto a Minifold II slot-blotter according to the procedure recommended by the manufacturer (Schleicher and Schuell) The equivalent of 10, 2, 0.4, 0.08, and 0.016 ul of culture were loaded together with previously quantitated standards of purified recombinant HIV-1 envelopes (Barr et al., *Vaccine* (1987), supra) and SODp31 (Steimer et al., (1986) supra), an hSOD fusion protein that contains a large portion of the HIV-1 integrase. The nitrocellulose was air-dried, washed overnight with RIBA kit wash buffer, and then probed for 30 min with pooled HIV positive sera from infected humans (1:200 dilution). Blots were developed using goat-anti-human antibodies conjugated to an enzyme label, and scanned using the reflective mode on a Shimadzu CS 9000 scanning densitometer. Peaks were integrated, compared with the appropriate standards, and approximate expression levels determined at 24 hr as shown in Table 1:

TABLE 1

| Recombinant Protein | Expression System | Expression level (mg/l) |
|---|---|---|
| env-4 | direct | 17 |
|  | hSOD fusion* | 35 |
|  | Ub fusion | 75 |
| env4-5 | direct | 6 |
|  | hSOD fusion | 7 |
|  | Ub fusion | 22 |
| HIV-1 integrase | direct | 28 |
|  | Ub fusion | 122 |

*A human superoxide dimutase (hSOD) fusion protein described in Barr et al., Vaccine (1987), supra.

Figure 3B:
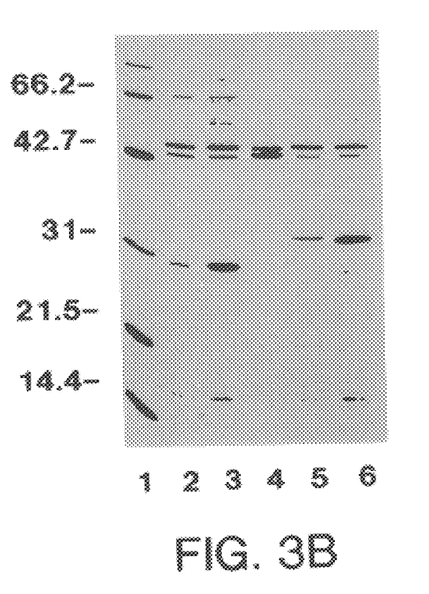
FIG. 3(b) provides in Lane 1, molecular weight standards; Lane 2 is directly expressed env4; Lane 3 is ubiquitin fusion-derived env4, clearly visible close to its calculated molecular weight of 27.1 kD; Lane 4 is hSOD-env4 fusion having a molecular weight of 42.9 kD; Lane 5 is directly expressed HIV-1 integrase; and Lane 6 is ubiquitin fusion-derived HIV-1 integrase of calculated molecular weight of 32.3 kD.

FIG. 3(*b*) provides the Coomassie blue stained SDS-PAGE results for the HIV-1 envelope polypeptide env4, and the HIV-1 integrase polypeptide. For env4, direct expression (lane 2) is low, whereas both ubiquitin fusion (lane 3) and hSOD fusion expression (lane 4) is considerably higher (see also Table 1). Similarly, for the longer envelope polypeptide env4–5, expression levels were significantly enhanced when the env4–5 gene was fused to either the ubiquitin or hSOD genes (Table 1). For HIV-1 integrase, direct expression was also compared with ubiquitin fusion expression. As evident from SDS-PAGE (FIG. 3(*b*); lanes 5 and 6) and quantitative immunoblot analysis (Table 1), the use of ubiquitin as an in vivo cleaved fusion partner for HIV-1 integrase clearly gives superior levels of viral protein production.

Although human gamma-IFN and alpha-1-AT have tertiary (Gln) and secondary (Glu) destabilizing amino acids respectively at their amino termini, it was shown earlier that the expressed products contain exclusively the amino acids predicted from the DNA sequence in this position. In contrast, as shown in Table 2, sequence analysis of env4 revealed that approximately 30% of the recombinant envelope polypeptide initiated with Glu. The remainder contained an additional Arg residue preceding the Glu residue predicted from the DNA sequence of the cleaved protein. Env4 is highly insoluble in yeast and can only be extracted using strong denaturants. It may be that the Arg-modified env4 protein by forming inclusion bodies becomes refractory to prokaryotic degradation, and thereby eventually constitutes the major portion of the isolated env4 product.

The amino terminus of virion-associated HIV-1 integrase has been shown to the $Phe_{716}$ of the pol open reading frame (Sanchez-Pescador et al., *Science* 227:484–492 (1986)). Phe belongs to the subset of amino acids that, when situated next to the initiation codon-derived Met residue, inhibit its removal by methionine aminopeptidase. Contrary to the likelihood that the directly expressed HIV-1 integrase retains this additional Met residue, sequence analysis of ubiquitin fusion-derived integrase gives an amino terminus of Phe exclusively.

TABLE 2

| Protein | Predicted Amino Terminal Amino Acid Sequence | Experimentally Determined Amino Terminal Amino Acid Sequence |
|---|---|---|
|  | 1 | 1 |
| hgamma-IFN | Gln.Asp.Pro . . . | Gln.Asp.Pro . . . 100% |
| alpha$_1$ AT | Glu.Asp.Pro . . . | Glu.Asp.Pro . . . 100% |
| env4 | Glu.Val.Val . . . | Arg.Glu.Val . . . 70% |
|  |  | Glu.Val . . . 30% |
| Integrase | Phe.Leu.Asn . . . | Phe.Leu.Asn . . . 100% |

Although the foregoing invention has been described in some detail for the purpose of illustration, it will be obvious that changes and modifications may be practiced within the scope of the appended claims by those of ordinary skill in the art.

I claim:

1. A method for expression in yeast of a heterologous protein to a level of at least 5% of total cell protein, wherein the protein comprises a destabilizing N-terminal amino acid residue selected from the group consisting of isoleucine, glutamic acid, histidine, tyrosine, glutamine, aspartic acid, asparagine, phenylalanine, leucine, tryptophan, lysine, and arginine, comprising:

(a) providing a DNA molecule encoding a ubiquitin fusion protein, said DNA molecule comprising a first DNA sequence that encodes ubiquitin and is immediately adjacent to, upstream of and in reading frame with a second DNA sequence that encodes the heterologous protein, wherein said first and second DNA sequences are operably linked to a promoter capable of promoting expression of the fusion protein to a level of at least 5% of total cell protein;

(b) transforming a yeast host cell with said DNA molecule; and (c) culturing the transformed yeast host cell under conditions capable of inducing the expression and quantitative in vivo processing of the fusion protein, thereby yielding expression of the heterologous protein to a level of at least 5% of total cell protein.

2. The method of claim 1 further comprising the step of recovering from the transformed cell culture, the heterologous protein free of ubiquitin.

3. The method of claim 1 wherein the heterologous protein is a mammalian or viral protein.

4. The method of claim 3 wherein the mammalian protein is selected from the group consisting of human alpha-1-antitrypsin, human gamma-interferon and human immunodeficiency virus integrase protein.

5. The method of claim 4 wherein the first codon of said nucleotide sequence encoding human alpha-1-antitrypsin encodes the amino acid glutamic acid.

6. The method of claim 4 wherein the first codon of said nucleotide sequence encoding human gamma-interferon encodes the amino acid glutamic acid.

7. The method of claim 4 wherein the first codon of said nucleotide sequence encoding the human immunodeficiency virus integrase protein encodes the amino acid phenylalanine.

8. The method of claim 1 wherein said yeast cell is from the genus Saccharomyces.

9. The method of claim 8 wherein said yeast cell is S. cerevisiae.

10. The method of claim 11 wherein the promoter is a regulatable promoter.

11. The method of claim 10 wherein the promoter is an ADH2-GAPDH hybrid yeast promoter.

12. The method of claim 11 wherein the N-terminal destabilizing amino acid residue is arginine.

13. The method of claim 11, wherein the N-terminal destabilizing amino acid residue is one selected from the group consisting of: lysine, phenylalanine, leucine, aspartic acid, asparagine, and tryptophan.

14. The method of claim 11, wherein the N-terminal destabilizing amino acid residue is one selected from the group consisting of: histidine, tyrosine, and glutamine.

15. The method of claim 11, wherein the N-terminal destabilizing amino acid residue is one selected from the group consisting of isoleucine and glutamic acid.

16. The method of claim 11, wherein the heterologous protein is an HIV-1 envelope polypeptide env4.

17. The method of claim 11, wherein the promoter is a promoter derived from a yeast glycolytic enzyme gene or a hybrid yeast promoter.

18. The method of claim 1, wherein the heterologous protein is a eukaryotic protein.

19. The method of claim 1, wherein the heterologous protein is a hormone or a growth factor.

20. The method of claim 1, wherein the heterologous protein is selected from the group consisting of growth hormone, somatomedins, epidermal growth factor, fibroblast growth factors, insulin, nerve growth factor, vasopressin, renin, calcitonin, erythropoietin, colony-stimulating factors, lymphokines and enzymes.

21. The method of claim 1, wherein the destabilizing N-terminal amino acid is authentic.

22. The method of claim 21, wherein the heterologous protein is expressed to a level of between about 5% and 50% of total cell protein.

23. The method of claim 22, wherein the heterologous protein is expressed to a level of between about 10% and 50% of total cell protein.

24. The method of claim 23, wherein the heterologous protein is expressed to a level of between about 10% to 30% of total cell protein.

25. The method of claim 22, wherein heterologous protein is expressed to a level of between about 5% and 30% of total cell protein.

26. The method of claim 25, wherein heterologous protein is expressed to a level of between about 5% and 10% of total cell protein.

27. The method of claim 11, wherein the heterologous protein is expressed to a level of between about 5% and 50% of total cell protein.

28. The method of claim 27, wherein the heterologous protein is expressed to a level of between about 10% and 50% of total cell protein.

29. The method of claim 28, wherein the heterologous protein is expressed to a level of between about 10% to 30% of total cell protein.

30. The method of claim 27, wherein heterologous protein is expressed to a level of between about 5% and 30% of total cell protein.

31. The method of claim 30 wherein heterologous protein is expressed to a level of between about 5% and 10% of total cell protein.

32. The method of claim 27 further comprising the step of recovering from the transformed cell culture, the heterologous protein free of ubiquitin.

33. The method of claim 27 wherein the heterologous protein is a mammalian or viral protein.

34. The method of claim 27 wherein the heterologous protein is selected from the group consisting of human alpha-1-antitrypsin, human gamma-interferon and human immunodeficiency virus integrase protein.

35. The method of claim 34 wherein the first codon of said nucleotide sequence encoding human alpha-1-antitrypsin encodes the amino acid glutamic acid.

36. The method of claim 34 wherein the first codon of said nucleotide sequence encoding human gamma-interferon encodes the amino acid glutamic acid.

37. The method of claim 34 wherein the first codon of said nucleotide sequence encoding the human immunodeficiency virus integrase protein encodes the amino acid phenylalanine.

38. The method of claim 27 wherein said yeast cell is from the genus Saccharomyces.

39. The method of claim 38 wherein said yeast cell is S. cerevisiae.

40. The method of claim 27 wherein the promoter is a regulatable promoter.

41. The method of claim 40 wherein the promoter is derived from a yeast glycolytic enzyme gene or a hybrid yeast promoter.

42. The method of claim 41 wherein the promoter is an ADH2-GAPDH hybrid yeast promoter.

43. The method of claim 27 wherein the N-terminal destabilizing amino acid residue is arginine.

44. The method of claim 27, wherein the N-terminal destabilizing amino acid residue is one selected from the group consisting of: lysine, phenylalanine, leucine, aspartic acid, asparagine, and tryptophan.

45. The method of claim 27 jwherein the N-terminal destabilizing amino acid residue is one selected from the group consisting of histidine, tyrosine, and glutamine.

46. The method of claim 27 wherein the N-terminal destabilizing amino acid residue is one selected from the group consisting of isoleucine and glutamic acid.

47. The method of claim 27, wherein the heterologous protein is an HIV-1 envelope polypeptide env4.

48. A DNA construct for expression in yeast of a heterologous protein having a destabilizing N-terminal amino acid residue selected from the group consisting of isoleucine, glutamic acid, histidine, tyrosine, glutamine, aspartic acid, asparagine, phenylalanine, leucine, tryptophan, lysine, and arginine, wherein the construct comprises a first DNA sequence that encodes ubiquitin and that is immediately adjacent to, upstream of and in reading frame with a second DNA sequence that encodes the heterologous protein, and wherein said first and second DNA sequences are operably linked to a promoter capable of promoting expression of the fusion protein to a level of at least 5% of total cell protein, wherein the fusion protein is capable of being quantitatively processed in vivo to yield the heterologous protein in yeast.

49. The DNA construct of claim 48, wherein the vector further comprises a transcription termination sequence located 3' to the second DNA fragment.

50. The DNA construct of claim 49, wherein the transcription termination sequence is the alpha-factor terminator.

51. The DNA construct of claim 49, wherein the transcription termination sequence is the GAPDH terminator.

52. The DNA construct of claim 48, wherein the promoter is a regulatable promoter.

53. The DNA construct of claim 52, wherein the regulatable promoter is an ADH2-GAPDH hybrid yeast promoter.

54. The DNA construct of claim 48, wherein the heterologous protein is a eukaryotic protein.

55. The DNA construct of claim 48, wherein the heterologous protein is a mammalian or a viral protein.

56. The DNA construct of claim 48, wherein the heterologous protein is a hormone or a growth factor.

57. The DNA construct of claim 48, wherein the heterologous protein is selected from the group consisting of growth hormone, somatomedins, epidermal growth factor, fibroblast growth factors, insulin, nerve growth factor, vasopressin, renin, calcitonin, erythropoietin, colony-stimulating factors, lymphokines and enzymes.

58. The DNA construct of claim 48, wherein the promoter is capable of promoting expression of the fusion protein to a level of betveen about 5% and 50% of total cell protein.

59. The DNA construct of claim 58, wherein the promoter is capable of promoting expression of the fusion protein to a level of betwveen about 10% and 50% of total cell protein.

60. The DNA construct of claim 59, wherein the promoter is capable of promoting expression of the fusion protein to a level of between about 10% to 30% of total cell protein.

61. The method of claim 58, wherein heterologous protein is expressed to a level of between about 5% and 30% of total cell protein.

62. The method of claimt wherein heterologous protein is expressed to a level of between about 5% and 10% of total cell protein.

63. A yeast host cell transformed by a vector that provides for expression of a heterologous protein having a destabilizing N-terminal amino acid residue selected from the group consisting of isoleucine, glutamic acid, histidine, tyrosine, glutamine, aspartic acid, asparagine, phenylalanine, leucine, tryptophan, lysine, and arginine, wherein the vector comprises a first DNA sequence that encodes ubiquitin and that is immediately adjacent to, upstream of and in reading frame with a second DNA sequence that encodes the heterologous protein, and wherein said first and second DNA sequences are operably linked to a promoter capable of promoting expression of the fusion protein to a level of at least 5% of total cell protein, and wherein the fusion protein is capable of being quantitatively processed in vivo to yield the heterologous protein.

64. The host cell of claim 63 wherein the yeast expression vector is a high copy number vector.

65. The yeast host cell of claim 63, wherein the yeast host cell is from the genus Saccharomyces.

66. The yeast host cell of claim 65, wherein the yeast host cell is *S. cerevisiae*.

67. The yeast host cell of claim 63, wherein the promoter is a regulatable promoter.

68. The yeast host cell of claim 67, wherein the regulatable promoter is an ADH2-GAPDH hybrid yeast promoter.

69. The yeast host cell of claim 63, wherein the heterologous protein is a eukaryotic protein.

70. The yeast host cell of claim 63, wherein the heterologous protein is a mammalian or a viral protein.

71. The yeast host cell of claim 63, wherein the heterologous protein is a hormone or a growth factor.

72. The yeast host cell of claim 63, wherein the heterologous protein is selected from the group consisting of growth hormone, somatomedins, epidermal growth factor, fibroblast growth factors, insulin, nerve growth factor, vasopressin, renin, calcitonin, erythropoietin, colony-stimulating factors, lymphokines and enzymes.

73. The yeast host cell of claim 63, wherein the promoter is capable of promoting expression of the fusion protein to a level of between about 5% and 50% of total cell protein.

74. The yeast host cell of claim 73, wherein the promoter is capable of promoting expression of the fusion protein to a level of between about 10% and 50% of total cell protein.

75. The yeast host cell of claim 74, wherein the promoter is capable of promoting expression of the fusion protein to a level of between about 10% to 30% of total cell protein.

76. The method of claim 73, wherein heterologous protein is expressed to a level of between about 5% and 30% of total cell protein.

77. The method of claim 76, wherein heterologous protein is expressed to a level of between about 5% and 10% of total cell protein.

* * * * *